(12) United States Patent
Thinket Selvan et al.

(10) Patent No.: US 11,983,468 B2
(45) Date of Patent: May 14, 2024

(54) SEALANT PROFILE SYSTEM AND METHOD

(71) Applicant: AIRBUS SAS, Blagnac (FR)

(72) Inventors: Arumugam Thinket Selvan, Toulouse (FR); Prakash Hatti, Karnataka (IN)

(73) Assignee: AIRBUS SAS, Blagnac (FR)

( * ) Notice: Subject to any disclaimer, the term of this patent is extended or adjusted under 35 U.S.C. 154(b) by 1601 days.

(21) Appl. No.: 16/172,652

(22) Filed: Oct. 26, 2018

(65) Prior Publication Data

US 2019/0130062 A1    May 2, 2019

(30) Foreign Application Priority Data

Oct. 27, 2017 (IN) .............................. 201741038237

(51) Int. Cl.
| | |
|---|---|
| *G06F 30/17* | (2020.01) |
| *B05C 11/10* | (2006.01) |
| *G01B 11/24* | (2006.01) |
| *B05C 5/00* | (2006.01) |
| *B29C 65/00* | (2006.01) |
| *G01N 33/00* | (2006.01) |

(52) U.S. Cl.
CPC .......... *G06F 30/17* (2020.01); *B05C 11/1021* (2013.01); *G01B 11/24* (2013.01); *B05C 5/00* (2013.01); *B29C 66/967* (2013.01); *G01N 2033/009* (2013.01)

(58) Field of Classification Search
CPC ..... G06F 30/00; G06F 30/17; B05C 11/1021; B05C 5/00; G01B 11/24; B29C 66/967; G01N 2033/009

USPC ......................................................... 703/7, 6
See application file for complete search history.

(56) References Cited

U.S. PATENT DOCUMENTS

| | | | |
|---|---|---|---|
| 4,884,697 A | 12/1989 | Takacs et al. | |
| 8,651,046 B1 | 4/2014 | Davancens et al. | |
| 2004/0005402 A1 | 1/2004 | Nesbitt | |
| 2007/0180674 A1* | 8/2007 | Morden | B21J 15/32 |
| | | | 29/407.01 |
| 2015/0081073 A1 | 3/2015 | Trautman et al. | |
| 2015/0241870 A1 | 8/2015 | Toh | |

FOREIGN PATENT DOCUMENTS

| | | |
|---|---|---|
| DE | 41 36 653 | 5/1993 |
| DE | 102 57 567 | 7/2004 |
| DE | 10 2006 018 558 | 10/2007 |
| EP | 2 647 951 | 10/2013 |
| EP | 3 072 599 | 9/2016 |

(Continued)

*Primary Examiner* — Cedric Johnson
(74) *Attorney, Agent, or Firm* — Nixon & Vanderhye P.C.

(57) ABSTRACT

A system and a method for determining a sealant profile to be applied by a sealant applicator, the applicator being arranged to apply sealant to the surface of a component. The system includes an imager configured to generate measurement data representing the surface of the component and a data receiver. The data receiver is arranged to receive the generated measurement data and predetermined component-related data. The system also includes a processor arranged to analyse the received data and to generate, based on the analysis, a sealant profile for application to the component, and a data output arranged to output data representing the generated sealant profile to the sealant applicator.

18 Claims, 3 Drawing Sheets

(56) References Cited

FOREIGN PATENT DOCUMENTS

| EP | 3 086 083 | | | 10/2016 | | |
|----|-----------|---|---|---------|---|---|
| GB | 2541547 | | | 2/2017 | | |
| GB | 2541547 | A | * | 2/2017 | ............... | B05B 1/30 |
| JP | 2016080695 | A | * | 5/2016 | ............. | B29C 73/22 |
| WO | WO-2009137051 | A2 | * | 11/2009 | ............... | B05D 5/00 |
| WO | 2014/042970 | | | 3/2014 | | |

* cited by examiner

SEALANT PROFILE SYSTEM AND METHOD

RELATED APPLICATION

This application claims priority to India patent application no. IN 201741038237 filed on Oct. 27, 2017, the entirety of which is incorporated by reference.

TECHNICAL FIELD

The present invention relates to a system and method for determining a sealant profile to be applied by a sealant applicator. The sealant applicator is arranged to apply sealant to the surface of a component.

BACKGROUND

Sealants are used in many industries, for example, in the construction, automotive and aerospace industries. They act as a type of mechanical seal to ensure air, water and fluid tightness between components or over the surface of a component, and may have adhesive qualities. Sealants are used in the manufacture of the structural parts, sub-assemblies and the final assembly of aircraft, in which requirements such as aerodynamic, waterproofing and corrosion-prevention exist. In practice, several hundred kilograms of sealant may be applied between aircraft parts at various levels of assembly. A sealant such as "interfay sealant" can be applied between one or more faying surfaces that contact one another. Sealant can also be applied over a surface as an overcoat to a fastener, at a fillet joint (in which sealant is applied over the intersection between surfaces that are approximately perpendicular to each other), or at a butt joint (in which sealant is applied between two approximately parallel substrate surfaces that are either edge-to-edge or face-to-edge).

Sealant can be applied to a surface using an applicator. Mechanical applicators that are guided by robotic arms are known; movement of these robotic arms can be automatically controlled using a computer program running on a computer. The use of a camera in conjunction with such a sealant applicator allows applied sealant to be inspected.

However, issues such as the curing of sealant as a function of time and the thickness of the applied sealant can interfere with the application of torque or other forces to fasteners that hold components together, for example screws, rivets or bolts, typically requiring re-tightening of fasteners that have already been used to assemble components between which interfay sealant has been applied. Manual labour is involved in preparing sealants having suitable requirements and manual application on large surface area parts may be required. Additionally, whether using a manual or automatic application, sealant is often applied too thickly or in areas where it is not necessarily required, and hardened sealant can become cracked or broken when fasteners are tightened. The application of excess sealant also leads to sealant wastage and the addition of unnecessary weight to the aircraft. Tightening or re-torqueing of fasteners and other adjustments to structural parts of the aircraft that are required following, and owing to, the application of sealant, can lead to degradation in the assembly quality, additional work and an increased manufacturing lead time.

SUMMARY

A first aspect of the present invention provides a system for determining a sealant profile to be applied by a sealant applicator, the applicator being arranged to apply sealant to the surface of a component, the system comprising: an imager configured to generate measurement data representing the surface of the component; a data receiver arranged to receive (i) the generated measurement data and (ii) predetermined component-related data; a processor arranged to analyse the received data and to generate, based on the analysis, a sealant profile for application to the component; and a data output arranged to output data representing the generated sealant profile to the sealant applicator.

Optionally, the imager can comprise a hyperspectral camera or a laser scanner. The imager may comprise one or more of an interferometer and an infrared focal plane array.

Optionally, the generated sealant profile is output to a controller of the sealant applicator, and the controller can be arranged to configure the sealant applicator to apply sealant to the component in accordance with the generated sealant profile.

Optionally, the data receiver may be configured to access one or more databases in which the pre-determined component-related data is stored, said data comprising one or more of aerodynamic requirements, design requirements, fastener torqueing requirements, and manufacturing requirements.

Optionally, in generating the sealant profile, the processor is arranged to determine one or more of an amount of sealant to be applied to the component, a thickness of sealant to be applied to the component, and a type of sealant to be applied to the component.

In one example, the component is a first component, and the imager can be configured to generate measurement data representing the surface of the first component and the surface of a second component that is to be joined to the first component by the sealant.

A second aspect of the present invention provides a computer-implemented method of determining a sealant profile to be applied by a sealant applicator, the applicator being arranged to apply sealant to the surface of a component, the method comprising the steps of: generating measurement data representing the surface of the component; receiving (i) the generated measurement data and (ii) predetermined component-related data; analysing the received data; generating, based on said analysing, a sealant profile for application to the component; and outputting data representing the generated sealant profile to the sealant applicator.

Optionally, generating the measurement data comprises performing hyperspectral imaging or laser scanning of the surface. Generating the measurement data may comprise imaging the surface using one or more of an interferometer and an infrared focal plane array.

Optionally, the method comprises outputting the data representing the generated sealant profile to a controller of the sealant applicator, and the controller can be arranged to configure the sealant applicator to apply sealant to the component in accordance with the generated sealant profile.

Optionally, the method comprises accessing one or more databases in which the pre-determined component-related data is stored, said data comprising one or more of aerodynamic requirements, design requirements, fastener torqueing requirements, and manufacturing requirements.

Optionally, generating the sealant profile comprises determining one or more of an amount of sealant to be applied to the component, a thickness of sealant to be applied to the component, and a type of sealant to be applied to the component.

In an example, the component is a first component, and the method can comprise generating measurement data representing the surface of the first component and the surface of a second component that is to be joined to the first component by the sealant.

A third aspect of the present invention provides a computer program, or a suite of computer programs, which, when executed by a processing system, causes the processing system to perform the above methods.

A fourth aspect of the present invention provides computer readable storage medium storing computer readable instructions thereon for execution on a computing system to implement the above methods.

A fifth aspect of the present invention provides a surface imaging system comprising an interferometer configured to detect spectral data from a surface, and a processor configured to: receive the spectral data and predetermined surface data; determine, from the received data, sealant requirements for the application of sealant to the surface; and output data indicative of said sealant requirements to a sealant applicator.

BRIEF DESCRIPTION OF THE DRAWINGS

Embodiments of the invention will now be described, by way of example only, with reference to the accompanying drawings, in which.

DETAILED DESCRIPTION

Figure 1A:
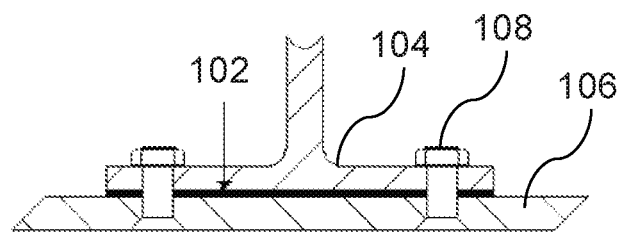
FIGS. 1a-1c show examples of surfaces and components to which sealant may be applied.
Figure 1B:
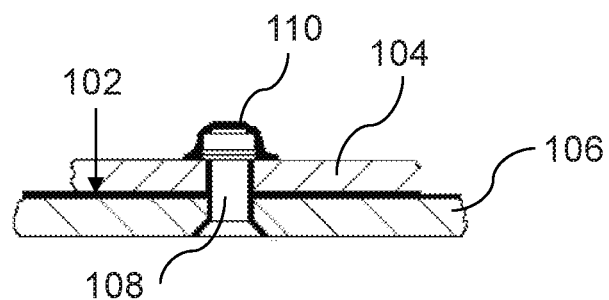
Figure 1C:
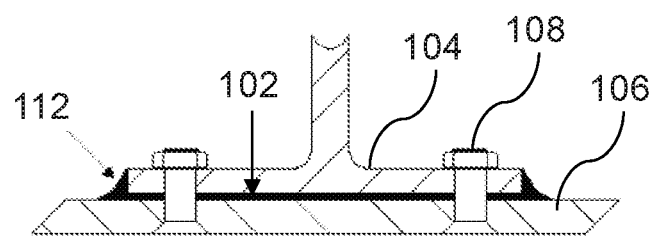

FIGS. 1a-1c show examples of surfaces and components to which sealant may be applied. FIG. 1a shows an example in which interfay sealant 102 is applied between a first component 104 and a second component 106. The sealant 102 can be applied to one or both of the surfaces of the first and second components before they are joined together, and one or more appropriately placed fasteners 108 are then used to securely assemble the components in place. FIG. 1b shows an example in which a layer of sealant is applied as an "overcoat" 110 to cover a fastener 108 that holds components 104 and 106 in place. Such an overcoat can protect the fastener 108 from the external environment. FIG. 1c shows an example of a sealant "fillet" 112 to cover the surfaces at the end of the joint at which components 104 and 106 are assembled. This fillet joint acts to reinforce the interfay sealant applied between components 104 and 106 and protects the edge of the interfay sealant section from the external environment.

Figure 2:
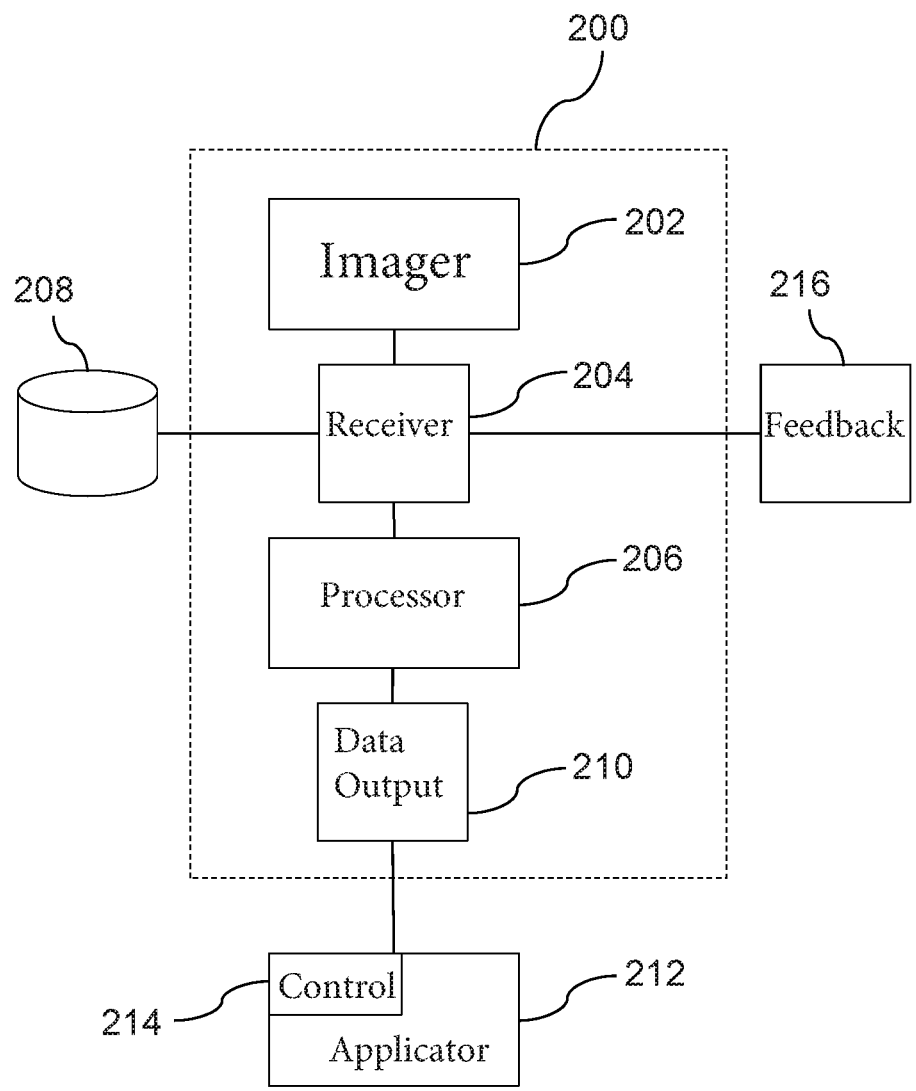
FIG. 2 shows a schematic view of a system for determining a sealant profile according to an example of the present invention.

FIG. 2 shows an example system 200 for determining a sealant profile. Such a sealant profile can be used to apply sealant in the situations shown in FIGS. 1a to 1c. The system 200, which can be referred to as a surface imaging system, has an imager 202 that is configured to generate measurement data representing a surface of one or more components (not shown). The imager 202 can be a hyperspectral camera or a laser scanner. The imager 202 can collect and process information from across the electromagnetic spectrum, for example by scanning the surface of the component or selected areas thereof. The imager 202 may include, for example, an interferometer such as a Michelson interferometer, and an infrared focal plane array to vary the imaging plane. The imager 202 provides measurement data in the form of spatially resolved spectral data about the surface of the component to which sealant is to be applied. Thus, the imager 202 provides measurement data of any surface imperfections and contours on the faying surface of imaged components.

The system 200 also has a communication interface, for example in the form of a data receiver 204 that is arranged to receive the measurement data that is generated by the imager 202. The data receiver 204 may be an input of a processor 206. The data receiver 204 also receives predetermined component-related data that is accessible from one or more databases 208. Database(s) 208 typically store design and engineering requirements that are related to the component to which sealant is to be applied. Database(s) 208 can also store design and engineering requirements of one or more components that are to be joined to the component to which sealant is to be applied. The design and engineering requirements can include data such as aerodynamic data, torqueing requirements of fasteners used to join components, manufacturing tolerances, and 3D models of components and their alignment with respect to one another. The predetermined component-related data may show the general shapes of surfaces and configurations of their required attachment to other components, but the surfaces are assumed to be smooth; data relating to surface imperfections and more detailed contours that are specific to the component surface(s) scanned by the imager are typically not provided in the predetermined component-related data.

The processor 206 receives the data that is input from the imager 202 and the databases 208 via the data receiver 204, and analyses the received data in order to generate a sealant profile for application to the component. The processor 206 does this by accurately calculating any gaps between the surfaces of components that are to be joined together. The imaged surface pattern can be compared to master surface data, such as a 3D image of the desired or optimal surface pattern from the database(s), which is used as a reference surface; such predetermined component-related data typically assumes a uniform surface and cannot take into account surface imperfections or potential gaps in specific surfaces. Various other requirements can be taken into account by the processor 206, in order to generate optimal sealing requirements of the sealant to be applied to the component in question. The sealant profile can include requirements of the sealant to be applied, including how the sealant should be applied to the surface in question in order to seal, cover, fill or join the surface as required.

The sealant profile can include one or more of an amount of sealant to be applied to the component, a thickness of sealant to be applied to the component, and a type of sealant to be applied to the component. The amount of sealant can be a volume or weight of sealant that is required. The type of sealant may be a wet sealant, a semi-cured sealant or a dry sealant; examples of sealants include polysulphide-based materials and polysilicon-based materials. Wet sealants may be applied by spraying a coating of sealant onto the surface(s). Although databases 208 may include suggested types of sealants for application to particular surfaces, the generated sealant profile may override this or suggest an alternative sealant based on the measurement data that is detected by the imager 202. A dry sealant may be provided as a tape or film with adhesive qualities, which can be applied in layers to a surface to give an accurate sealant thickness. The sealant may be a UV or heat curable form-in-place dry film application, in which the film takes on the contours of the component surface and fills any voids in the surface contours according to the sealant profile. The required thickness of sealant over different areas of the surface will vary depending on factors such as surface imperfections and the torqueing requirements of fasteners present on or between surfaces.

In an example, the processor 206 may be configured to calculate the difference, or variations, between the measured data and the surface design data obtained from the database 208, for example by using 3D geometry and subtracting one of the respective sets of surface data from the other. The calculated variations can then be converted by the processor into a sealant volume or thickness to be applied to appropriately defined areas of the surface(s); in order to do this, the processor 206 may obtain, for example from database 208, sealant characteristics such as viscosity, curing characteristics and typical or ideal sealant amounts in respect of a particular part or type of seal (e.g. interfay, overcoat, fillet, etc.).

The system 200 has a data output 210 that is connected to or part of the processor 206, and that is arranged to output data representing the generated sealant profile to a sealant applicator 212. The data can be output directly to a controller 214 of the sealant applicator 212. In one example, the controller is arranged to cause the sealant applicator to apply sealant to the component in accordance with the generated sealant profile. The controller 214 may form an integral part of, or may be operatively connected to, the sealant applicator 212. The output data may comprise instructions for the controller 214, such that the controller 214 is able to implement the instructions to apply the sealant according to the sealant profile. In an alternative example, the controller 214 may be part of the system 200 and/or the processor 206, such that the system 200 can use the generated sealant profile to directly control application of the sealant to the relevant components. In yet another example, the processor 206 can act as a controller by outputting data representing the sealant profile in the form of instructions to the sealant applicator 212; in this example the controller 214 of the sealant applicator 212 may be, for example, a robot configured to receive the instructions and control movement and/or sealant flow of the sealant applicator 212.

In one example, the imager 202 generates measurement data of the surface of two or more components that are to be joined together by interfay sealant. Together with information from database(s) 208 regarding the way in which the components are intended to fit together, the processor 206 can precisely measure any gaps that will occur between the surfaces of the components owing to contours and surface imperfections, and can generate a sealant profile that allows the system to optimise the amount of sealant applied to different areas of one or more of the surfaces.

By generating a sealant profile for the application of sealant to one or more surfaces, the system 200 allows the final assembly requirements, together with any torqueing/tightening requirements, of fasteners, to be met. Wastage of sealant and time and labour spent applying sealant or removing excess sealant are also reduced or eliminated. The thickness of the sealant is optimised, so that the sealant thickness is uniform where required, and the risk off applying excess sealant, and hence the overall weight of the aircraft, is reduced.

The system 200 can be used in conjunction with a feedback system 216 that assesses the applied sealant using, for example, one or more electro-optic, visual, infrared or ultrasonic sensors, detectors or cameras. The processor 206 can use this information to analyse whether the sealant has been applied as determined by the sealing profile generated. If re-application is required in certain areas, this can be determined and instructed by the processor 206. Cleaning of any excess sealant may be automatically instructed by the processor 206 and carried out by a separate sealant cleaning system (not shown) after any feedback has taken place.

Figure 3:
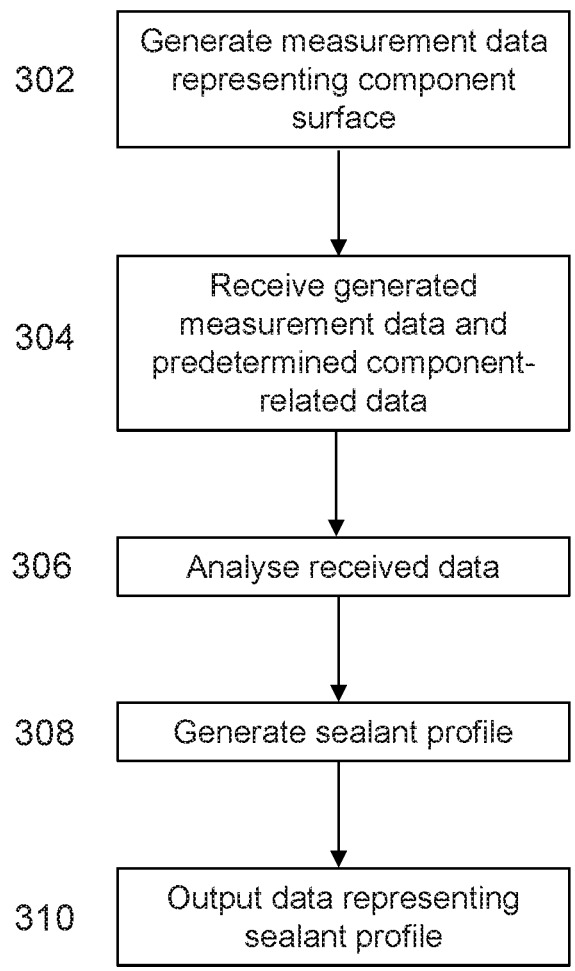
FIG. 3 shows a flowchart of a method of determining a sealant profile according to an example of the present invention.

FIG. 3 shows a flowchart of a method 300 of determining a sealant profile using a system such as the surface imaging system 200 of FIG. 2. At step 302, measurement data representing the surface of one or more components is generated by the imager 202. This may include the surface to which sealant is to be applied, together with any other surfaces of parts that are to be attached to the component.

At step 304, the generated measurement data is received by data receiving means 204, which may be input means of the processor 206. Predetermined component-related data, such as is explained above with respect to FIG. 2, is also received from one or more databases 208.

At step 306, the processor 206 analyses the data received at step 304, and at step 308 a sealant profile is generated based on the analysed data. At step 310, data representing this sealant profile, i.e. data indicative of the sealant requirements for sealant to be applied to the imaged surface(s), is output from the processor 206 or other data output 210 of the system 200. The sealant profile can be output to a controller 214 of a sealant applicator 212. Alternatively, the processor 206 can act as a controller by outputting data representing the sealant profile in the form of instructions to the sealant applicator 212.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A system for determining an interfay sealant profile to be applied by an interfay sealant applicator, the applicator being arranged to apply an interfay sealant to a first surface of a component, the system comprising:
   an imager configured to generate measurement data representing the first surface of the first component and a second surface of a second component, wherein the first surface is configured to be placed on the second surface to form a joint between the first component and the second component with the interfay sealant between the first and second surfaces;
   a data receiver configured to receive the generated measurement data and predetermined component-related data;
   a processor configured to analyse the received data and to generate, based on the analysis, an interfay sealant profile for application to the first surface of the first component, wherein the interfay sealant profile indicates at least one of:
      an amount of the interfay sealant to be applied to the first and/or second components, a thickness of the interfay sealant to be formed between the first and second components, or a type of sealant as the interfay sealant to be applied to the first and/or second components; and a data output arranged to output data representing the generated interfay sealant profile to the interfay sealant applicator before application of the interfay sealant on the first surface.

2. The system of claim 1, wherein the imager comprises a hyperspectral camera or a laser scanner.

3. The system of claim 1, wherein the imager comprises one or more of an interferometer and an infrared focal plane array.

4. The system of claim 1, wherein the generated interfay sealant profile is output to a controller of the interfay sealant applicator, said controller being arranged to configure the interfay sealant applicator to apply interfay sealant to the first surface of the first component and/or the second surface of the second component in accordance with the generated interfay sealant profile.

5. The system of claim 1, wherein the data receiver is configured to access one or more databases in which the pre-determined component-related data is stored, said pre-determined component-related data comprising one or more of aerodynamic requirements, design requirements, fastener torquing requirements, and manufacturing requirements.

6. The system of claim 1 wherein, in generating the interfay sealant profile, the processor is arranged to determine an amount of interfay sealant to be applied to the first surface of the first component and/or to the second surface of the second component.

7. The system of claim 1 wherein, in generating the interfay sealant profile, the processor is arranged to determine a thickness of interfay sealant to be applied to the first surface of the first component and/or to the second surface of the second component.

8. The system of claim 1 wherein, in generating the interfay sealant profile, the processor is arranged to determine a type of interfay sealant to be applied to the first surface of the first component and/or to the second surface of the second component.

9. The system of claim 1, wherein the interfay sealant profile is for application to the first surface to the second surface before the first component is joined to the second component.

10. A computer-implemented method of determining an interfay sealant profile to be applied by an interfay sealant applicator, the applicator being arranged to apply interfay sealant to a first surface of a first component, the method comprising:

generating measurement data representing the first surface of the first component and a second surface of a second component to be joined to the first component by the interfay sealant;

receiving the generated measurement data and predetermined component-related data;

analyzing the received generated measurement data and the predetermined component related data;

generating, based on said analyzing, an interfay sealant profile for the interfay sealant to be applied to the first surface and/or second surface, wherein the interfay sealant profile indicates at least one of:

an amount of the interfay sealant to be applied to the first and/or second surfaces, a thickness of the interfay sealant to be formed between the first and second surfaces, or a type of sealant to be applied as the interfay sealant to the first and/or second surfaces; and outputting data representing the generated interfay sealant profile to the interfay sealant applicator before the interfay sealant is applied to the first surface.

11. The method of claim 10, wherein generating the measurement data comprises performing hyperspectral imaging or laser-based scanning of the first surface and of the second surface.

12. The method of claim 10, wherein generating the measurement data comprises imaging the first surface and the second surface using one or more of an interferometer and an infrared focal plane array.

13. The method of claim 10, comprising outputting the data representing the generated interfay sealant profile to a controller of the interfay sealant applicator, said controller being arranged to configure the interfay sealant applicator to apply interfay sealant to the first surface and/or the second surface in accordance with the generated interfay sealant profile.

14. The method of claim 10, comprising accessing one or more databases in which the pre-determined component-related data is stored, said data comprising one or more of aerodynamic requirements, design requirements, fastener torquing requirements, and manufacturing requirements.

15. The method of claim 10, wherein:

the interfay sealant profile is for application of the interfay sealant to the first surface and/or the second surface before the first component is joined to the second component.

16. The method of claim 10, further comprising the applicator dispensing the interfay sealant to the first surface and/or the second surface, wherein the interfay sealant is formed by the applicator to conform to the generated interfay sealant profile.

17. A non-transitory computer readable storage medium storing computer readable instructions thereon for execution by a computing system, wherein the computer readable instructions, when executed by the computing system, instruct the computing system to carry out a method of determining an interfay sealant profile to be applied by an interfay sealant applicator, the interfay sealant applicator being arranged to apply an interfay sealant to a first surface of a first component and/or a second surface of a second component, wherein the first and second surfaces are configured to be brought together to form a joint between the first and second components, the method comprising:

causing to be generated measurement data representing measurements of the first surface of the first component and measurements of the second surface of a second component, receiving the generated measurement data and predetermined component-related data;

analyzing the received generated measurement data and the predetermined component-related data;

generating, based on said analyzing, an interfay sealant profile for application to the first surface of the first component, wherein the interfay sealant profile indicates at least one of:

an amount of the interfay sealant to be applied to the first and/or second surfaces, a thickness of the interfay sealant to be formed between the first and second surfaces, or a type of sealant to be applied as the interfay sealant to the first and/or second surfaces; and outputting data representing the generated interfay sealant profile to the interfay sealant applicator before the applicator applies the interfay sealant to the first and/or second surfaces.

18. An assembly system comprising:

an imager configured to generate measurement data representing a first surface of a first component and a second surface of a second component, wherein the first and second surfaces are to be brought together to form a joint between the first and second components;

a data receiver configured to receive the generated measurement data and predetermined component-related data;

a processor configured to analyze the received generated measurement data and the predetermined component-related data, and to generate, based on the analysis, an interfay sealant profile for the interfay sealant to be applied to the first and/or second surfaces, wherein the interfay sealant profile indicates at least one of:
  an amount of the interfay sealant to be applied to the first and/or second surfaces,
  a thickness of the interfay sealant to be formed between the first and second surfaces, or
  a type of sealant to be applied as the interlay sealant to the first and/or second surfaces;

a data output arranged to output data representing the generated interfay sealant profile to the interfay sealant applicator before the interfay sealant is applied to the first and/or second surface, and an interfay sealant applicator configured to dispense an interfay sealant onto the first and/or second surface, wherein applicator is configured to form and/or apply the interfay sealant to conform to the interfay sealant profile.

\* \* \* \* \*